Oct. 18, 1949. K. SAWADA Plant Pat. 884
PYRACANTHA PLANT
Filed Aug. 7, 1948
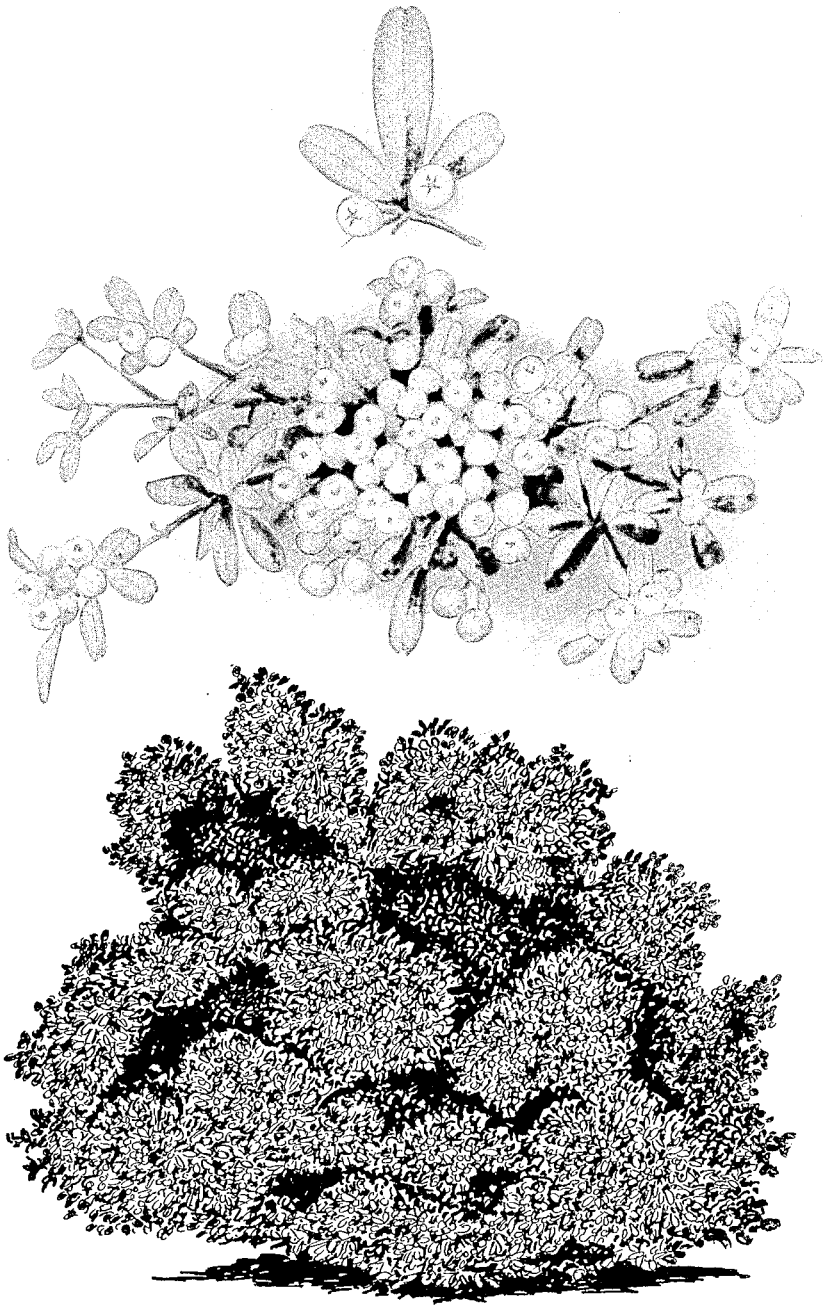
WITNESS
Addison F. Avery
INVENTOR
KOSAKU SAWADA,
by Rommler, Rommler & Snow,
ATTYS.

Patented Oct. 18, 1949

Plant Pat. 884

UNITED STATES PATENT OFFICE

884

PYRACANTHA PLANT

Kosaku Sawada, Crichton Station, Ala., assignor, by mesne assignments, to Overlook Nurseries, a corporation of Alabama Application August 7, 1948, Serial No. 43,131

1 Claim. (Cl. 47—60)

This invention relates to a new and distinctly improved variety of Pyracantha plant that has particularly attractive features for use as an ornamental shrub.

This variety has been developed for the densely compact dwarf character of its growth with prolific evergreen foliage, its brilliant and abundant array of red berries which stay on the branches all winter, and the absence of thorns.

The original plant was a sport of *Pyracantha koidzumii* (Formosana) discovered by me in 1941 and has been extensively reproduced asexually by cutting and grafting. The original eight-year old plant is now 4½ feet in height and has a 5½ foot spread.

In the drawing, Figure 1 is a side view showing the typical form and proportions of a field-grown plant of the new variety; Fig. 2 shows in color the characteristic arrangement of the leaves and berries viewed from the end of a branch; Fig. 3 shows full sized details of the leaves and berries.

This new Pyracantha does not resemble any existing variety and is distinguished from its known parent and another well-known variety as indicated in the following table:

| New Variety | *P. koidzumii* (Formosana) | *P. yunnanensis* |
|---|---|---|
| very dwarf, globe shape. | very tall, spreading branches. | low with very spreading branches. |
| small size leaf, firmer | larger leaves in every respect. | leaves narrow and long. |
| thornless | very thorny | very thorny. |
| berry large | berry larger | berry smaller in size. |
| coral red | coral red | coral red. |
| Ripe, October to November. | ripe, October to November. | ripe, 2 or 3 weeks later. |

As grown in Alabama, the coloring of the plant is indicated by Maerz & Paul's Dictionary of Color, as follows:

| | Plate | Letter | No. |
|---|---|---|---|
| Main red of berry | 1 | L | 7 |
| into | 1 | L | 8 |
| Main green of leaf | 23 | L | 10 |
| Back of leaf | 21 | L | 8 |
| Stem, gray | 45 | A | 1 |
| to brown | 56 | H | 1 |

Distinguishing characteristics are as follows:

Parentage: Sport.

Parent variety: *Pyracantha koidzumii* (Pyracantha Formosana).

Classification: *Pyracantha koidzumii* var. Sawada's Thornless Dwarf Globe.

It is the result of definite breeding efforts carried on by me since 1941.

It has been reproduced asexually from cuttings and grafting.

Eight-year old plant is now 4½ feet in height, 5½ foot spread. Size: very dwarf; and spreading.

Foliage: Heavy.

*Length.*—Most foliage ¾ inch long and ⅜ inch wide; some is 1½ inches long and ½ inch wide.

*Color.*—Upper surface, shiny green; under surface, pale green.

*Shape.*—Obovate to oblong-obovate or spatulate; margin entire, apex normally emarginate.

Stems:

*Size.*—Small and slender.

*Color.*—Gray to grayish brown.

*Growth.*—Short but slender and very thick growth.

*Texture.*—Very fine.

Branches (angles of attachment): Alternate; horizontal to about 20°. Some have pendulous tendency.

Twigs: Young twigs are grayish green to reddish green in color. Pubescent on tender twigs.

Bloom: Blooms last part of March around Mobile, Ala.

*Flower buds.*—On short peduncles in lateral cymes which are 1½ inches across.

*Calyx.*—Color—light green. Size—$\frac{1}{16}$ to ⅛ inch.

*Petals.*—Shape—5 orbicular petals ($\frac{3}{16}$ inch long), usually notched at apex. Color—white.

*Anthers.*—Shape—irregular. Color—brownish yellow. Pollen—very fine. Color—yellow.

*Filaments.*—Shape—threadlike. Color—yellowish white.

*Pistils.*—Shape—cylindrical; divided at top to 5 stigmas. Color—yellowish green.

Berry:

*Outside.*—Size—$\frac{3}{16}$ to ¼ inch long. Cavity—regular. Color—coral red. Flavor—apple-like. Shape—globose to urceolate, slightly flattened. Bears regularly.

*Inside.*—Flesh, color—creamy white. Juicy—no. Texture—meat coarse and dry. Productive—no. Skin—thick. Suture—very shallow, or none.

Seeds:

*Size.*—$\frac{1}{16}$ in. long x $\frac{1}{32}$ in. wide.

*Shape.*—Irregular rectangular.

*Number.*—5.

*Color.*—Black.

*Ripening period.*—Berries turn red in October-November; stay all winter; have no food value.

*Disease and pest resistant.*—Sometimes attacked by red spider and thrips.

This variety is unique in its low and compactly spreading growth which gives it a distinctively globose contour, the firm texture and small size of its evergreen leaves, the abundance of variously sized masses of red berries, appearing against the green background of its foliage, and the complete absence of thorns.

I claim:

The new and distinct variety of *Pyracantha koidzumii* plant shown and described, characterized by its dwarf globular growth, its distinctive foliation and absence of thorns.

KOSAKU SAWADA.

No references cited.